United States Patent [19]

Hartranft

[11] Patent Number: 4,623,328
[45] Date of Patent: Nov. 18, 1986

[54] PUMP MONITOR FOR PHOTOACTIVATION PATIENT TREATMENT SYSTEM

[75] Inventor: Thomas P. Hartranft, Safety Harbor, Fla.

[73] Assignee: McNeilab, Inc., Fort Washington, Pa.

[21] Appl. No.: 665,826

[22] Filed: Oct. 29, 1984

[51] Int. Cl.⁴ .......................... A61M 1/03; G01D 5/34
[52] U.S. Cl. .................................. 604/4; 250/231 SE
[58] Field of Search .............. 101/93.29, 93.30, 93.31, 101/93.32, 93.33, 93.36; 250/231 SE; 417/42, 63; 604/4, 5, 6; 235/98 C, 104

[56] References Cited

U.S. PATENT DOCUMENTS

| | | | |
|---|---|---|---|
| 3,814,934 | 6/1974 | Mesh | 250/231 SE |
| 3,886,354 | 5/1975 | Swiden | 250/231 SE X |
| 4,398,906 | 8/1983 | Edelson | 604/6 |
| 4,447,191 | 5/1984 | Bilstad | 417/63 X |
| 4,498,983 | 2/1985 | Bilstad | 604/6 X |

Primary Examiner—Harland S. Skogquist
Attorney, Agent, or Firm—Mark A. Hofer

[57] ABSTRACT

A preferred patient blood treatment system for the photoactivation of reagents in contact with a patient's blood employs an infusion pump for adding anti-coagulation reagent to the blood during extracorporeal operations. The infusion pump is preferably driven by a stepper motor and monitored by a periodic photo chopper employing a plurality of sensors. The spacing of the sensors and the spacing of the photo choppers work in concert to detect rotation of the stepper motor and to discriminate such from stutter or other characteristic nonrotational faults associated with stepper motors.

5 Claims, 5 Drawing Figures

PUMP MONITOR FOR PHOTOACTIVATION PATIENT TREATMENT SYSTEM

FIELD OF THE INVENTION

This invention relates to the field of treating cells with photoactivatable compounds and radiation which activates the compound thereby affecting the cells and specifically, relates to clinically useful systems for the extracorporeal treatment of blood cells, especially leukocytes, with UV radiation, and most particularly to a stepper motor anticoagulation reagent infusion pump monitor.

BACKGROUND OF THE INVENTION

It is well-known that a number of human disease states may be characterized by the overproduction of certain types of leukocytes, including lymphocytes, in comparison to other populations of cells which normally comprise whole blood. Excessive or abnormal lymphocyte populations result in numerous adverse effects to patients including the functional impairment of bodily organs, leukocyte mediated autoimmune diseases and leukemia related disorders many of which often ultimately result in fatality.

U.S. Pat. Nos. 4,321,919; 4,398,906; 4,428,744; and 4,464,166 to Edelson describe methods for treating blood whereby the operation or viability of certain cellular populations may be moderated thereby providing relief for these patients. In general, the methods comprise treating the blood with a dissolved photoactivatable drug, such as psoralen, which is capable of forming photoadducts with DNA in the presence of U.V. radiation. It is believed that covalent bonding results between the psoralen and the lymphocyte nucleic acid thereby effecting metabolic inhibition of the thusly treated cells. Following extracorporeal radiation, the cells are returned to the patient where they are thought to be cleared by natural processes but at an accelerated pace believed attributable to disruption of membrane integrity, alteration of DNA within the cell, or the like conditions often associated with substantial loss of cellular effectiveness or viability.

Although a number of photoactivatable compounds in the psoralen class are known, 8-methoxy psoralen is presently the compound of choice. An effective radiation for this compound, and many psoralens in general, is the ultraviolet spectrum in the range of approximately 320 to 400 nanometers, alternatively referred to as the U.V.A. spectrum. As the development of photoactivatable compounds proceeds, it may be expected that changes in the preferred activation radiation spectrum will be necessary. Suitable selection of radiation sources will, of course, increase treatment efficiency and is contemplated as an obvious optimization procedure for use with the inventions disclosed herein.

Although Edelson's methods have been experimentally shown to provide great relief to patients suffering from leukocyte mediated diseases, numerous practical problems remained requiring solutions. In particular, Edelson fails to provide a suitable apparatus for applying radiation to the cells, e.g. via a treatment station, in an economical and efficacious manner, or a system for incorporating a treatment station providing for the treatment of a patient in a clinically acceptable format.

Conventional techniques for photoactivating compounds associated with cells have relied on a plurality of devices including flasks, filtration columns, spectrophotometer cuvettes, and petri dishes. The sample to be irradiated is added to the containers and the container placed adjacent to the radiation source. Such systems tend to be laboratory curiosities as they fail to provide the necessary safeguards intrinsically necessary where patient bodily fluids are concerned, particularly since these fluids must be returned to the patient thereby necessitating strict avoidance of contamination. Further, such methods tend to be volume limited, are characterized by many mechanical manipulations and are generally unacceptable from a clinical and regulatory viewpoint. It is an object of the present invention to provide methods and apparatus suitable for use with the Edelson methods to overcome the limitations associated with the conventional expedients.

Copending application U.S. Ser. No. 650,602 of Taylor describes a preferred form of a practical device for coupling the radiation provided by commercially available light sources, such as the so-called "black-light" fluorescent tubes, to cells for treatment by Edelson's photoactivated drug methods. In summary, the disposable cassette described therein comprises a plurality of fluorescent tube-like light sources such as the U.V.A. emitting Sylvania F8TS/BLB bulb, which are individually, coaxially mounted in tubes of larger diameter which are, in turn, coaxially mounted in sealing arrangement within second outer tubes of even larger diameter thereby forming a structure having two generally elongated, cylindrical cavities about each radiation source. The inner cavity preferably communicates with the atmosphere thereby facilitating cooling of the radiation source. The second tube forming the outer cavity further comprises inlet and outlet means for receiving and discharging, respectively, the cells to be irradiated. A plurality of these structures are "ganged" and suitable connections made between inlets and outlets of adjacent members to provide for serpentine flow of cells through each outer cavity. Thus, continuous flow of the cells through the plurality of cavities surrounding the centrally disposed radiation sources facilitates thorough treatment of the cells. Additional, detailed description of the Taylor device may be obtained by direct reference to U.S. Ser. No. 650,602, the relevant aspects of which are fully incorporated herein by reference.

To be fully practical, however, the Taylor device requires a clinically acceptable instrument to house the device and to provide the cells to be treated in an appropriate form. It is an object of the present invention to provide such a device.

To date and for clinical use-approval related purposes, the Edelson methods have been performed utilizing a generally impractical and unwieldy apparatus consisting of a large, desk-size metal box containing a series of flexible, relatively transparent plastic bags through which patient blood was pumped. As the blood flowed through each bag, it was irradiated on either side by a plurality of ultraviolet emitting, standard sized, "fluorescent" type tubes housed within the box. Blood flow was generated by means of a separate pump located nearby and connected to the plastic bags as well as source and drain reservoirs by flexible tubing.

Prior to treatment, it has been found preferable to perform leukocyte enriching operations for the purpose of removing substantial portions of red blood cells from the treatment circuit. With the preliminary experimental apparatus, leukocyte enrichment was obtained by centrifuging batch quantities of blood in large volume centrifuge tubes and then dispensing the supernatant plasma into the source bag for treatment. Thus, the Edelson methods have been carried out to date via a cumbersome series of labor intensive, error-prone steps, often exposing the patient's blood to numerous potential sources of contamination during its travels to and from equipment, none of which was designed to optimize the Edelson procedures. Excessive time delays and extensive mechanical manipulations were further exacerbated by the typically divergent locations of various pieces of equipment, necessitated by their space consuming construction. These considerations have resulted in lengthy treatment times and, due to the numerous physical manipulations required, have concommittantly and unacceptably increased the risk of loss or contamination of patient's blood.

It is an object of the present invention to provide methods and apparatus for increasing patient safety thereby also raising his comfort level as well as meeting regulatory acceptability standards.

It is another related object to provide a complete treatment system which contains all the elements necessary for the withdrawal, separation, and treatment of the patient's blood in a compact and clinically acceptable size and to provide the system in a mobile and automated format thereby reducing the risk of inadvertent contamination while concurrently facilitating the ease with which treatment may be given.

It is still another related object to provide a suitably automated instrument which can be monitored and operated by less trained personnel thereby lowering treatment costs in accordance with the recently enacted fiscal policies.

It is yet still another related object to provide a treatment system suitable for use in the clinical arena whereby the acceptability of the Edelson procedures may be augmented so that a greater number of patients may be meaningfully treated.

BRIEF DESCRIPTION OF THE DRAWINGS

These and still other objects of the invention will become apparant upon study of the accompanying drawings wherein.

SUMMARY OF THE INVENTION

In accordance with the principles and objects of the present invention there is provided a stepper motor pump monitor for use with methods for extracorporeally photoactivating a photoactivatable reagent in contact with blood cells comprising the steps of collecting and separating on a continuous basis blood from a patient while the patient is connected to the apparatus, returning undesired blood portions obtained during separation, disconnecting the patient from the treatment system while the desired portion is photoactivatably treated whereupon the thusly treated cells are returned to the patient.

The various aspects of such photoactivation treatment are accomplished safely by breaking the entire procedure down into three stages or modes. The apparatus, in the first mode or phase, collects and separates blood on a continuous basis as it is withdrawn from the patient and to return unwanted portions to the patient while the patient remains connected to the apparatus. Thereafter, prior to energizing the irradiation sources for photoactivating the photoactivatable reagent in contact with the desired blood portion, the patient is disconnected from the machine thereby physically and electrically isolating him (or her) from the energizing high voltages, a potential source of harm. Following photoactivation, the treated cells may then be facilely returned to the patient utilizing a variety of techniques, the preferred being a simple drip chamber gravity feed infusion line.

Figure 1:
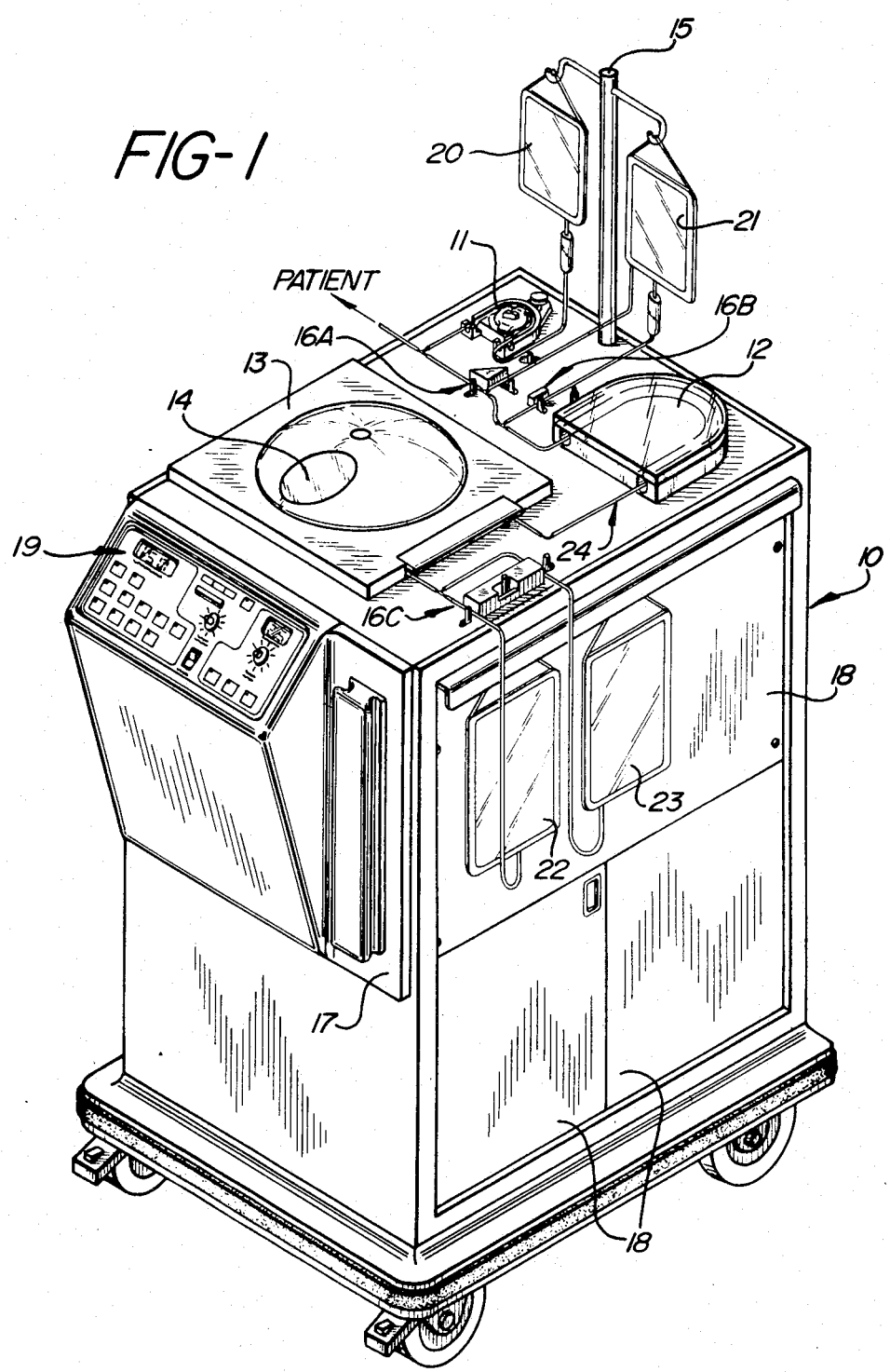
FIG. 1 illustrates a preferred configuration of the system in the collection and separation mode.
Figure 2:
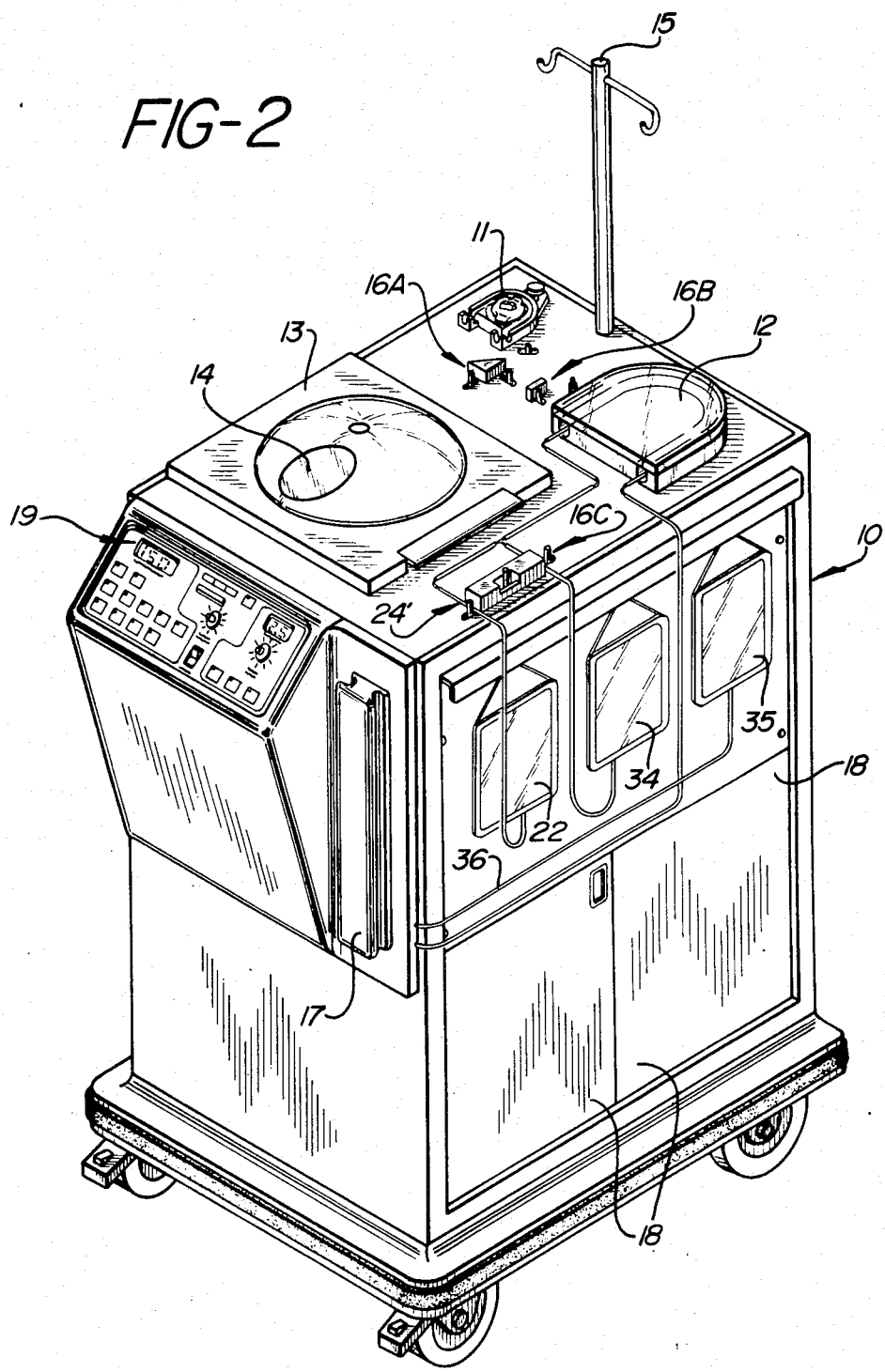
FIG. 2 depicts the system in the treatment mode.
Figure 3:
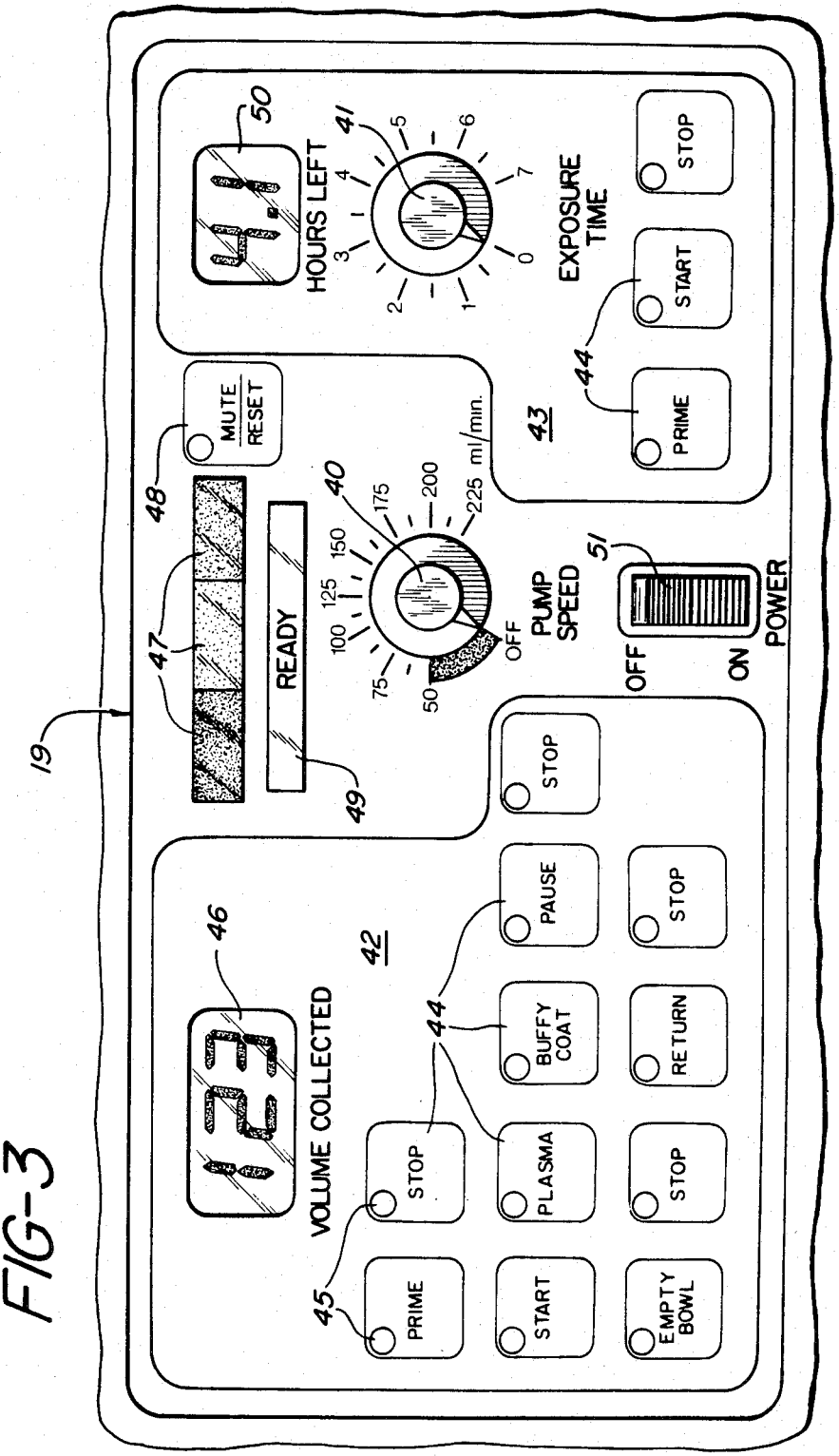
FIG. 3 shows the control panel for the system.

FIGS. 1, 2, and 3 show various aspects of the apparatus developed by the assignee hereof for extracorporeally treating a patient based in part upon the scientific discoveries of Edelson. The design, construction and operation of the apparatus 10 is the result of a number of separate inventions some of which form the subject matter of copending commonly assigned applications including U.S. Ser. No. 665,834 to Goss entitled "Three Phase Irradiation Treatment Process"; U.S. Ser. No. 665,831 to King entitled "Electronic Control Methods for Puvaphoresis Apparatus"; U.S. Ser. No. 665,827 to Troutner entitled "Valve Apparatus for Photoactivation Patient Treatment System"; U.S. Ser. No. 665,832 to King entitled "Automated Photophoresis Blood Portion Control Methods and Apparatus"; U.S. Ser. No. 665,833 to King et al. entitled "Patient Photophoresis Treatment Apparatus and Method"; and U.S. Ser. No. 665,817 to Troutner entitled "Cassette Drawer Assembly for Photoactivation Patient Treatment System", the relevant parts of which are fully incorporated herein by reference.

The operation of the device and performance of the methods can be divided into three basic phases or modes, depicted in part by FIGS. 1 and 2. The first phase is shown substantially in FIG. 1 wherein the patient is connected at the point shown such as by venipuncture or the like methods well-known and developed to a high degree in the dialysis arts. Patient blood, as it flows to the apparatus 10 (alternately referred to herein as the puvaphoresis apparatus or system) is preferably infused, under control of pump 11, with an anticoagulation agent contained in container 20 hung from stand 15. Control of the flow of patient blood to the remainder of apparatus 10 is controlled largely by clamping means 16a which has the dual function of also controlling flow in the reverse direction as well as flow to return container 21; clamp 16a acting as an "or" valve. Normally the blood flows through tubing 24 through blood pump 12 into a continuous centrifuge 13. This continuous centrifuge, available commercially from suppliers such as Dideco and others, is preferably capable of continuously separating blood based on the differing densities of the individual blood components. "Continuously", as used herein means that, as blood flows into the centrifuge through line 24, it accumulates within the rotating centrifuge bowl and is separated so that low density components are emitted after a certain minimum volume has been reached within the centrifuge bowl and as additional blood is added. Thus, the continuous centrifuge in effect acts as a hybrid between a pure online system and a pure batch system. This occurs because the centrifuge bowl has a capacity to capacity to hold most, if not all, of the most dense portion, typically erythrocytes or red blood cells while emitting lower density portions such as plasma and leukocytes (white blood cells) as whole blood is continuously added. At some point, however, the reservoir volume of the centrifuge is filled with the higher density components and further separation cannot be effectively obtained.

Prior to that point, the operator, by viewing the uppermost portion of the centrifuge bowl through magnifying observation point port 14 of the centrifuge cover, can detect qualitatively when the centrifuge emits plasma (as opposed to priming solution), leukocyte enriched portions and nonleukocyte enriched portions such as erythrocytes. Based on the operator's observations, he or she enters through control panel 19 (specifically via panel portion 42) the identification of the individual blood portions as they are emitted from the centrifuge. Based on this information, entered by keys 44 (e.g. PLASMA, BUFFY COAT or leukocyte enriched portion) on control panel 19 (FIG. 3), apparatus 10 controls valve mechanism 16c to direct the leukocyte enriched portion and a predetermined volume of plasma into plasma-leukocyte enriched container 22 while excess plasma, air, priming fluids, erythrocytes etc. are directed to container 23.

Once the centrifuge is no longer capable of further separation due to the attainment of its capacity, the operator directs that the bowl be emptied (see FIG. 3) by suitable data key entry whereupon the contents of container 23 and centrifuge 13 are advantageously pumped into return container 21 by means of pump 12 under the control of valves 16a and c. The foregoing steps may be repeated a number of times or cycles before the desired volume of leukocyte enriched blood and plasma is obtained for further treatment, in each instance the undesired portions being first collected in container 23 and then pumped to return container 21.

Between cycles, the erythrocyte enriched portion which is pumped into return bag 21 is gravity fed back to the patient through a drip infusion operation and controlled by valve 16b. It is preferred that gravity feed be employed rather than pumping the blood back to the patient via pump 12 in order to avoid potential pressurization problems at the infusion insertion site at the patient, and also to avoid foaming or other air related dangers.

As may be already appreciated, when initially set up, line 24 may be expected to contain sterilized air which is preferably removed by suitable priming operations utilizing the anti-coagulation agent in container 20; both the air and the priming solution being collected in container 23.

Also to be noted is the predetermination of the leukocyte enriched volume and plasma volume to be collected within container 22 as well as the number of cycles to be employed to collect same. These volumes are selected largely in accordance with the individual volume capacities of the containers as well as the treatment cassette to be described later. Accordingly, these volumes are chosen in order to preferably optimize handling efficiency and to ensure patient safety. For instance, one preferred selection would include the settings: 250 ml total buffy coat or leukocyte enriched portion and 300 ml of plasma to be collected within container 22. This might require any number of cycles preferably on the order of say three or four bearing in mind that the more cycles that are selected, the lower the total volume of blood withdrawn from the patient at any one time, within minimum capacity limits of the centrifuge bowl, thus increasing the patient's capacity to withstand temporary blood volume depletions and the treatment procedure in general. Alternately, more cycles will also permit more discriminating selection of leukocyte enriched blood as it is emitted from the centrifuge. The buffy coat and plasma volumes as well as the number of cycles are typically physician selected and accordingly, the controls governing the selections are preferably placed within the apparatus 10, such as behind doors 18 where their inadvertent alteration may be avoided especially since no operator interaction is generally required with respect to these data inputs.

Referring now to FIG. 2, a second tubing set for the second operating mode of apparatus 10 is shown with leukocyte enriched container 22 connected via tubing line 24' through valve 16c, blood pump 12 to the treatment cassette assembly 17 with a return line 36 to reservoir container 35. The tubing set for the second mode will also preferably include container 34 for providing a priming solution for evacuating air contained within tubing set 24' and the cassette treatment module, described in copending application of Taylor, U.S. Ser. No. 650,602. In brief summary, Taylor cassette comprises a plurality of ganged cylindrical cavities each of which is concentrically mounted around a cylindrical irradiation source in turn powered by apparatus 10.

In operation, and with respect to FIG. 3, the exposure time on the right hand portion of the panel 43 is set in accordance with physician determined criteria via knob 41. The central control means of the apparatus 10, calculates and displays (50) via central processing unit and memory stored software, the exposure time remaining at the onset of irradiation treatment and as the treatment progresses. Section 43 of the control panel also includes three operator controlled entry data keys 44 whereby the first step, PRIME, may be initiated whereupon the priming solution from container 34 is pumped via blood pump 12 through tubing set 24' and the treatment cassette emptying into reservoir 35. Thereafter, the operator, by pushing START in section 43, initiates actual photoirradiation treatment whereupon the leukocyte enriched portion of the blood, collected within container 22, is pumped through tubing set 24' in accordance with suitably altered valve 16c, through blood pump 12 to the treatment cassette, and return line 36 to reservoir 35.

The treatment cassette container assembly 17 further comprises air bubble detectors on the tubing to and from the cassette for generating a signal responsive to the presence of air, said signals being conveyed to the central control means for signaling the presence of air about to enter the treatment cassette. The presence of the air indicates the evacuation of container 22 and signals the end of the first treatment pass. Thereafter, the central control means reverses the direction of blood pump 12 which draws blood from container 35 back through the treatment cassette through the blood pump and to container 22. The actual direction of the blood flow through the treatment cassette is of no significance as flow in either direction is equally photoactivated. An advantage gained by reversing direction (as opposed to constant cycling in the same direction) is the hydrodynamic mixing of blood as it is passed through the container. Such mixing is thought to result in a more thorough treatment of the individual cells because the statistical probability that each cell will be individually contacted by irradiation is increased. This process of blood flow until container 22 or 35 is emptied and then reversal thereof is continued until the desired exposure time is attained. At that point, the treated blood portion is then preferably returned to blood container 22 and the tubing set 24' discarded.

Container 22 is then ideally removed to stand 15 and a third tubing set connected to container 22 for reinfusion of the treated blood portion into the patient. During the second operational mode when the actual irradiation treatment is performed as depicted by FIG. 2, the patient is preferably disconnected from the machine thereby adding to his (or her) comfort level by permitting him freedom to move about but also concommitantly, increasing his safety level as he (or she) is not connected to the machine when the high voltages, necessary to drive the irradiation sources, are present.

To further decrease the risk of contamination to the patient blood and blood portions, each time a connection is made or broken, it is preferably only done once. Thus, container 22 would have three connection ports; one for the first mode collection of the leukocyte enriched blood portion, one for the second mode treatment phase shown by FIG. 2, and the third set for the third mode wherein treated blood is reinfused to the patient.

With particular reference to FIG. 3, the control panel 19 of the apparatus 10 is shown with the key board entry buttons 44 each ideally having a light 45 which, when lit, preferably indicates the stage of the operation. As will be noted, the key board entry buttons 44 are preferably placed in sequential order thereby assisting the operator in learning the system and performing the steps in the correct order. Indeed, the central control means will preferably be programmed to prevent out of step sequences from being attempted. Display 46 indicates the volume of leukocyte enriched blood collected in container 22. Although not shown, there is preferably also included a manual override switch contained within apparatus 10 such as behind access doors 18 (see FIGS. 1 and 2) for allowing an experienced operator to select any step out of sequence in the unlikely circumstance that such may be necessary to return all blood to the patient in the event of a machine failure.

The central portion of panel 19 contains power switch 51 as well as blood pump speed control 40 whereby the operator may select the speed with which the blood is withdrawn from the patient and pumped through the system during either collection or treatment phases. Also included in the central section are lights 47. Alphanumeric display 49 indicates alarms and status regarding the machine's sequential operations. Status lights 47 are preferably provided in green, yellow, and red colors in order to provide at a glance the overall operating status of apparatus 10. Further included is a mute reset button 48 for quieting an audible alarm activated in the event an alarm condition occurs and operator input is required.

Other features may be readily apparent from the drawings such as the preferable inclusion of casters and caster brakes for enhancing the mobility of the apparatus. Further, upper access door 18 will preferably include mechanical means for assisting in the securement of containers 22, 23, 34, and 35. It may also optionally be outfitted with a transparent or translucent opening in the area beneath container 22 for providing at a glance information regarding the illumination status of the irradiation treatment cassette during the treatment phase. For instance, if the window is of sufficient size, the operator may readily determine that each irradiation source within the treatment cassette is illuminated as desired. Naturally, the material comprising such window is preferably selected in order to contain harmful radiation, if any, within apparatus 10.

The aforedescribed photophoresis blood treatment apparatus is made largely possible by automated control methods for directing the blood portions derived from the continuous centrifuge into particular containers. The automated methods perform in accordance with preset volume determinations which are manually entered pursuant to a physician's direction. These predetermined volumes specify the volume to be contained within the buffy coat or leukocyte enriched container 22 by setting forth the volume of plasma and the volume of leukocyte enriched blood portion to be contained therein. Additionally included within these condition setting parameters is preferably the ability to set forth the number of cycles of blood collection and separation required or desired in order to obtain the desired blood volumes.

The volumes collected are determined in accordance with the blood volume pumped by the blood pump. This may be suitably monitored and communicated to the central control means by specifically monitoring the speed of the blood pump rotation. Rotation may be conveniently monitored such as by attachment of a slotted disk to the shaft and the passage of slots determined by an optical or other electrical or mechanical sensor means. The resultant periodic signal may be conveniently correlated with speed of rotation by circuit designs well-known in the art. The rotational speed coupled "with the known volume pumping characteristics of the pump, will provide the necessary information to permit calculation of the volume of blood pumped.

In actual operation, the ideal procedure would be as follows. The operator primes the tubing set, the blood pump, and the centrifuge with the anti-coagulant solution contained in container 20. Thereafter, blood is withdrawn from the patient and pumped by the blood pump into the rotating centrifuge. As the blood enters the centrifuge, it displaces the priming solution which emerges first in accordance with its preferably lighter density. This priming solution is automatically directed into container 23. At some point, the priming solution will be completely displaced from the rotating centrifuge and plasma will begin to emerge. This emergence may be directly observed through port 14 whereupon the operator presses the PLASMA key on control panel section 42. Thereafter, the central control means automatically directs the plasma into container 22 keeping track of the volume as it does so. This continues until either the operator indicates the leukocyte enriched portion, i.e. buffy coat has begun by pressing the respective data entry key in control panel section 42 whereupon, the leukocyte enriched portion continues to container 22, however, the volume so directed is monitored as buffy coat volume. Alternately, if all of the predetermined plasma volume is collected prior to the emergence of the buffy coat, then the central control means automatically diverts, by valve 16c, the emerging plasma fluid stream to container 23. In that instance, upon the emergence of the buffy coat and the keying of the BUFFY COAT data entry switch 44, the central control means diverts the emerging buffy coat into container 22 again keeping track of its volume since the volume pumped into the centrifuge equals the volume energizing therefrom.

The collection of the buffy coat will continue preferably in accordance with both the predetermined buffy coat volume as well as the number of cycles, also a predetermined condition by the physician. If this most preferred embodiment is employed, then a representative example might be as follows. Assume, that the predetermined volume and cycle conditions are set as follows: 350 mls of plasma, 250 mls of buffy coat, and 5 cycles. In each cycle, the apparatus will collect 250/5 or 50 mls of buffy coat before ending the cycle and thereupon emptying the centrifuge bowl and returning predominantly erythrocytes and perhaps excess plasma to the patient. Prior to the collection of the 50 mls, plasma will emerge from the centrifuge and will be collected in container 22 either until the full 350 mls are collected or, until the buffy coat emerges.

During the next cycle, the central control means will direct the further collection of plasma, if needed, in order to reach the 350 ml predetermined volume and then collect an additional 50 mls of buffy coat. The total volume to be contained within container 22, will then equal 600 mls and would be indicated on display 46 as it is accumulated.

Thus, the central control means of the apparatus automatically keeps track of the volumes as they are collected thereby facilitating the institution of a convenient number of cycles whereby the removal of large blood volumes from the patient is avoided. Not only is patient safety enhanced thereby, but the automated nature of the procedure further increases safety since, in accordance with the programmed data supplied to the central control means, the operator need not attempt to keep track of plasma and leukocyte enriched volumes, while still being assured that the final solution for treatment will contain the predetermined and desired leukocyte concentration.

As previously indicated, the most preferred embodiment of the photoactivatable patient treatment system includes container 20 for providing an anti-coagulation agent to the patient's blood as it is obtained from the patient. This may be advantageously accomplished by connecting container 20 to the tubing connected to the patient and controlling the flow from container 20 by means of an infusion pump 11. Although there are a variety of pumps and pump drive mechanisms available for this task, it has been found preferable to employ a peristaltic or roller type pump which is suitable for high precision, low volume delivery. Further, it has been found preferable to drive this pump by means of a stepper motor which, due to its nature, can drive the pump in a highly variable, incremental fashion thereby providing a great control regarding the rate of anti-coagulation reagent or priming solution delivery from bag 20. Indeed, it has been found desirable to rotate the infusion pump 11 at a rate of approximately 1 turn per 10 turns of the blood pump.

Stepper motors have, however, the undesirable characteristic of sometimes failing to advance after receiving a signal to do so in a mode of action that can be best described as "stuttering". Like cardiac fibrillation, such stuttering fails to deliver fluid volume and is accordingly undesirable.

Most mechanisms useful for gaging the rate of rotation employ some type of light chopping mechanism such as by rotating protrusions, ribs, tabs, or reflective lines past a stationary light source whereby the blocking or unblocking of the light from the light source to a photodetector creates a signal related to the rate of motor shaft rotation. Clearly, given known pumping characteristics of a pump, e.g. volume per rotation, in combination with the number of shaft revolutions for the pump motor, the volume being delivered at any particular time may be easily calculated. Unfortunately, it was found that such optical chopper devices are incapable of identifying stepper motor stutter and instead interpret the stuttering as constant rotation thereby providing signals which are erroneously interpreted to mean volume delivery when such is not the case.

The instant invention overcomes the limitations of known chopper devices inasmuch as the instant invention not only provides a signal responsive to stepper motor shaft rotation speed but, also provides signals which indicate when such rotation is really stuttering, i.e. a sequential forward and backward rotation without net forward rotation.

Figure 4:
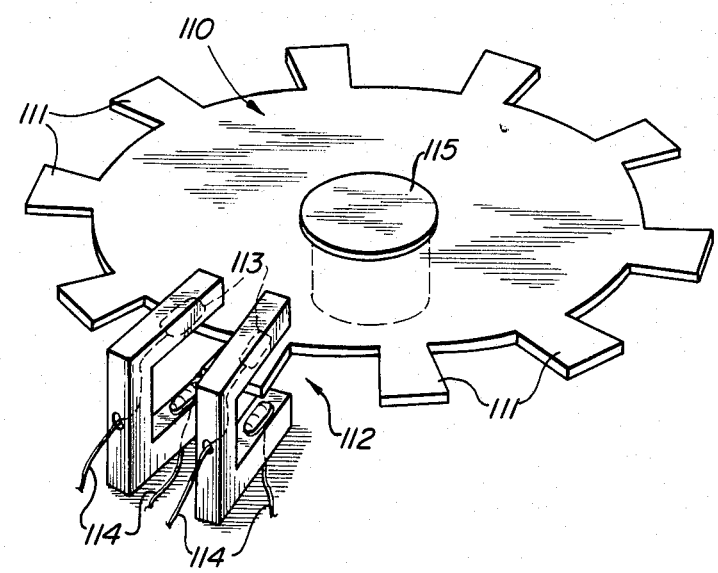
FIG. 4 shows a perspective view of the preferred configuration of the stepper motor pump monitor.
Figure 5:
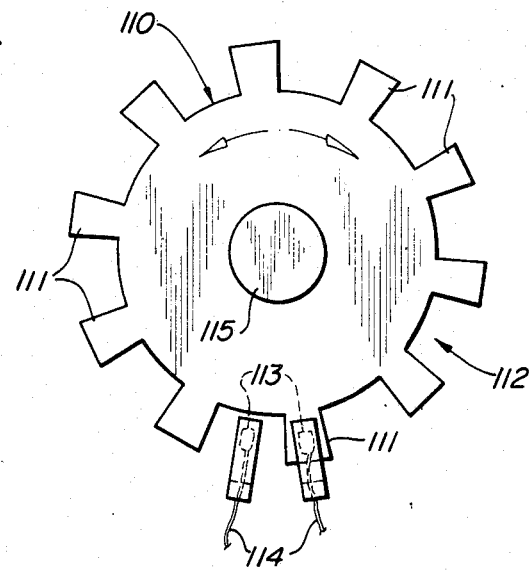
FIG. 5 shows a top view of the FIG. 4 monitor.

Understanding will be assisted by reference to FIGS. 4 and 5 which show the stepper motor monitor of the instant invention. Attached to the stepper motor output shaft 115 is a periodic blocking means 110 shown as a disk having protruding tabs 111 at the periphery thereof. Also shown are two sensors 113 for sensing the presence or absence of tabs 111 and generating a signal conveyed by wires 114 to the central control system. Although sensors 113 show an illumination source and a detection source whereby the passage of light therebetween is blocked by the presence of tab 111, other obvious alternatives may be readily had such as the placement of source and detector on the same side, and the presence of tab 111 serving to reflect the light to the detector thereby generating an inverse signal (e.g. positive signal for presence versus positive signal for absence of tab 111) as compared to the shown arrangement.

The instant invention is capable of discriminating the stuttering due to the employment of multiple sensors in combination with the unique spacing characteristics of tabs 111 versus spaces 112. Examination of FIG. 5 will clearly show that the preferred embodiment utilizes a space 112 having an area approximately twice that of the area per tab 111. Further, it will be noted that the spacing of sensors 113 and their size are carefully regulated so that one sensor constantly remains unblocked, i.e. over a space 112, while the other sensor may also be in a space 112 or as shown, over a tab 111. Signals from leads 114 are accepted alternately by the central processing control system so that information regarding continued rotation is ensured. Thus, if one sensor provides an "on" signal, the next signal that must be received is an "off" signal from the other sensor. Stuttering of the stepper motor, would result in a repetition of the first "on" signal prior to receiving a "off" signal and thus, such a failure would be immediately detectable. Alternatively, under proper conditions, the continuous receipt of on/off signals from altering sensors would indicate the desired continuous rotation of the stepper motor and thus the delivery of solution through the infusion pump connected thereto.

It should be carefully noted, that although spaces 112 are shown to be twice the area of tabs 111, the exact reverse situation is equally contemplated herein, e.g. tabs 111 being twice the area of spaces 112 and the sensors 113 being suitably arranged so that one is always blocked by the now larger tab while the other may be blocked or unblocked. In this alternative arrangement, it will now be readily apparent that the signals generated by the sensors will be the inverse of those previously described, however, such signals may easily be handled electronically by well-known methods.

One skilled in the art may readily appreciate that variations to the size and spacing of the spaces, tabs and location of the sensors may be made without departing from the spirit or scope of the instant invention.

What is claimed is:

1. A stepper motor monitor for use in a blood treatment system for photoactivating extracorporeally a photoactivatable reagent in contact with a patient's blood, said system including an infusion pump driven by a shaft from a stepper motor, said monitor comprising:
   periodic blocking means mounted on said stepper motor shaft for rotation therewith; and
   at least two sensors for generating a signal responsive to the periodicity of said blocking means, said sensors being stationary with respect to said periodic blocking means and arranged whereby one sensor is always unblocked and both sensors must be unblocked before one sensor can become blocked and in accordance with the said signals generated the rate or absence of stepper motor shaft rotation may be determined.

2. The monitor as provided in claim 1 wherein said periodic blocking means is a disk possessing periodically spaced tabs protruding from the periphery of said disk.

3. The monitor as provided in claim 2 wherein said sensors comprise a source of illumination and illumination detection means whereby a signal is generated responsive to the passage of the protruding tab.

4. The monitor as provided in claim 3 wherein the area of the space between said protruding tabs is approximately twice the area of the tab and the sensor covers no more area than that of the tab.

5. In an extracorporeal blood treatment system for the photoactivation of a reagent in contact with said blood including a stepper motor driven fluid pump, a pump shaft speed and rotation monitor comprising a disk fixedly mounted on said pump shaft, said disk having periodic cutouts about said periphery thereby forming periodic tabs and at least two sensors fixedly mounted with respect to said tabs for generating a signal in accordance with the presence or absence of a tab and wherein said sensors are spaced in relation to said tabs whereby said sensors may be affected by the same space and may be separated by a tab, but are never separated by a space or affected by the same tab.

* * * * *